(12) United States Patent
Geng et al.

(10) Patent No.: US 11,505,734 B2
(45) Date of Patent: *Nov. 22, 2022

(54) NONIONIC GEMINI SURFACTANT OF (OCTYLPHENOL POLYOXYETHYLENE ETHER DISUBSTITUTED) DICARBOXYLIC ACID DIPHENYL ETHER AND ITS SYNTHESIS METHOD

(71) Applicant: PetroChina Company Limited, Beijing (CN)

(72) Inventors: Xiangfei Geng, Beijing (CN); Bin Ding, Beijing (CN); Jianhui Luo, Beijing (CN); Bo Huang, Beijing (CN); Jianyong Xie, Beijing (CN); Pingmei Wang, Beijing (CN); Yongcan Peng, Beijing (CN); Baoliang Peng, Beijing (CN)

(73) Assignee: PetroChina Company Limited, Beijing (CN)

( * ) Notice: Subject to any disclaimer, the term of this patent is extended or adjusted under 35 U.S.C. 154(b) by 391 days.

This patent is subject to a terminal disclaimer.

(21) Appl. No.: 16/691,942

(22) Filed: Nov. 22, 2019

(65) Prior Publication Data

US 2020/0208044 A1    Jul. 2, 2020

(30) Foreign Application Priority Data

Jan. 2, 2019   (CN) .......................... 201910001670.8

(51) Int. Cl.
  *C09K 8/584*   (2006.01)
  *C09K 8/60*    (2006.01)
  *C07C 67/08*   (2006.01)
  *C07C 69/76*   (2006.01)

(52) U.S. Cl.
  CPC ............. *C09K 8/604* (2013.01); *C07C 67/08* (2013.01); *C07C 69/76* (2013.01); *C09K 2208/06* (2013.01)

(58) Field of Classification Search
  CPC .... C09K 8/604; C09K 2208/06; C09K 8/584; C07C 67/08; C07C 69/76; C07C 67/14; C07C 69/92; C08G 65/337
  See application file for complete search history.

(56) References Cited

U.S. PATENT DOCUMENTS

| | | | |
|---|---|---|---|
| 3,627,845 A | 12/1971 | Hickner et al. | |
| 5,900,397 A * | 5/1999 | Tracy | C07C 45/71 510/505 |
| 6,204,297 B1 * | 3/2001 | Tracy | C09K 23/00 568/22 |
| 2011/0220839 A1 | 9/2011 | Wong et al. | |
| 2018/0024434 A1 | 1/2018 | Takemura et al. | |
| 2019/0177491 A1 | 6/2019 | Zhou et al. | |

FOREIGN PATENT DOCUMENTS

| | | |
|---|---|---|
| CN | 101108326 A | 1/2008 |
| CN | 102993413   | 3/2013 |
| CN | 103127744 A | 6/2013 |
| CN | 104830301   | 8/2015 |
| CN | 107304162   | 10/2017 |
| CN | 107663449 A | 2/2018 |
| CN | 108114617 A | 6/2018 |

(Continued)

OTHER PUBLICATIONS

C A.Bunton, L.Robinson. Catalysis of nucleophilic substitutions by micelles of dicationic detergent [J]. F. J. Org. Chem, 1971(36): 2346-2352.

(Continued)

*Primary Examiner* — Kumar R Bhushan
(74) *Attorney, Agent, or Firm* — Meunier Carlin & Curfman LLC

(57) ABSTRACT

A nonionic Gemini surfactant, (octylphenol polyoxyethylene ether disubstituted) dicarboxylic acid diphenyl ether has a structural formula of:

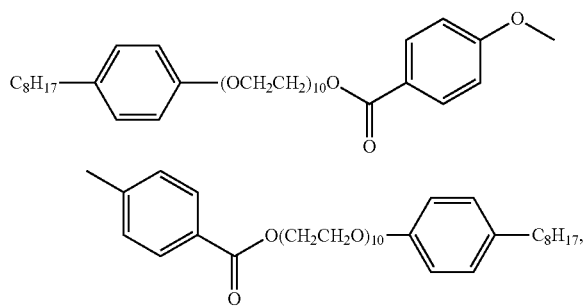

and is prepared by a two-step reaction: S1, diphenyl ether 4,4'-dicarboxylic acid is subjected to an acyl chlorination reaction to obtain diphenyl ether 4,4'-dicarbonyl dichloride; S2, diphenyl ether 4,4'-dicarbonyl dichloride is subjected to an esterification reaction with octylphenol polyoxyethylene ether (OP-10) to obtain the target product (octylphenol polyoxyethylene ether disubstituted) dicarboxylic acid diphenyl ether. The surfactant is expected to be applied in tertiary oil recovery as an alkali/surfactant, in polymer/surfactant binary composite flooding, in alkali/surfactant/polymer ternary composite flooding, as a microemulsion emulsifier and the like, and it can also be compounded with a common surfactant to reduce the use cost, and thus create conditions for its large-scale application.

1 Claim, 3 Drawing Sheets

(56) References Cited

FOREIGN PATENT DOCUMENTS

JP      2017141212         8/2017
WO     2017151159 A1      9/2017

OTHER PUBLICATIONS

Y.P.Zhu, A. Masuyama, Deinega, Preparation and properties of double-or-triple-chain surfactants with two sulfonate groups derived from N-acyldiethanolamines [J]. J. Am. Oil Chem. Soc, 1991(68): 539-543.
Zhu Y P, Masuyama A, Okahara M. Preparation and surface active properties of amphipathic compounds with two sulfate groups and two lipophilic alkyl chains [J] J Am Oil Chem Soc,1990, 67(7): 459-463.
Zhu. Y P, Masuyama A, Kirito M. Preparation and surface-active properties of new amphipathic compounds with two phosphate groups and two long-chain alkyl groups [J] J Am Oil Chem Soc, 1991, 68(4): 268-271.
Menger F M,Littau CA. Gemini surfactants: synthesis and properties[J]. J. Am Chem Soc, 1991(113): 1451-1452.
Rosen, MJ. Geminis: A new Generation of surfactants. [J] J Chem Technol, 1993(30): 23-33.
Zana R,Talmon Y. Dependence of aggregate morphology on structure of dimeric surfactants. [J] Nature, 1993(362): 228-229.
Shen Zhiqin et al; "Synthesis and Properties of Nonionic-anionic Gemini Surfactants with High Activity", Advances in Fine Petrochemicals, vol. 12, No. 9; dated Jun. 1, 2011; 5 pages.

\* cited by examiner

NONIONIC GEMINI SURFACTANT OF (OCTYLPHENOL POLYOXYETHYLENE ETHER DISUBSTITUTED) DICARBOXYLIC ACID DIPHENYL ETHER AND ITS SYNTHESIS METHOD

CROSS-REFERENCE TO RELATED APPLICATION

This application claims priority to Chinese Patent Application No. 201910001670.8, filed on Jan. 2, 2019, which is hereby incorporated by reference in its entirety.

TECHNICAL FIELD

The invention relates to the field of surfactants, in particular to a nonionic Gemini surfactant of (octylphenol polyoxyethylene ether disubstituted) dicarboxylic acid diphenyl ether and synthesis thereof.

BACKGROUND

In 1971, Bunton et al studied the surface activity of p-alkylene-bis (alkyl dimethyl ammonium bromide) $[CmH_{2m+1}N^+(CH_3)_2-(CH_2)_5-C_mH_{2m+1}N^+(CH_3)_2]Br^-_2$, and investigated the properties of these surfactants when the linking groups were hydrophilic, hydrophobic, flexible and rigid groups, respectively (C. A. Bunton, L. Robinson. Catalysis of nucleophilc substituions by micelles of dieationic detergent W. F. J. Org. Chem, 1971(36): 2346-2352). In 1974, Deinega et al synthesize a group of novel amphiphilic molecules, having a molecular structure in order of: long hydrocarbon chain, ionic head group, linking group, a second ionic head group, and a second hydrocarbon chain (Y. P. Zhu, A. Masuyama, Deinega, Preparation and properties of double-or-triple-chain surfactants with two sulfonate groups devised from N-acyldiethanolamines [J]. J. Am. Oil Chem. Soc, 1991(68): 539-543). In the early 1990s, Okahara et al in Osaka University in Japan synthesized a variety of anionic Gemini surfactants with flexible groups as linker, and their properties were investigated (Zhu Y P, Masuyama A, Okahara M. Preparation and surface active properties of amphipathic compounds with two sulfate groups and two lipoplulic alkyl chains [J] J Am Oil Chem Soc,1990, 67(7): 459-463; Zhu. Y P, Masuyama A, Kirito M. Preparation and surface-active properties of new amphipathic compounds with two phosphate groups and two long-chain alkyl groups [J] J Am Oil Chem Soc, 1991, 68(4): 268-271; Zhu Y. P, Masuyama A, Kiriito Y. Preparation and properties of double or triple-chain surfactants with two sulfonate groups derived from N-acyldiethanulamines [J] J Am Oil Chem Soc, 1991, 68(7) 539-543). However, systematic and purposeful studies on these new surfactants began in 1991 with the work of Menger and Lihua in the University of Emery. They synthesized and studied a bis-alkane chain surfactant with a rigid group as linker and named it Gemini (which means Gemini in astronomy) surfactant, (Menger F M, Littau C A. Gemini surfactants: synthesis and properties [J]. J. Am Chem Soc, 1991(113): 1451-1452). Both the Rosen group and the Zana group accepted the designation, and a large number of targeted studies have been carried out (Rosen, M J. Geminis: A new Generation of surfactants. [J] J Chem Technol, 1993(30): 23-33; Zana R, Talmon Y. Dependence of aggregate morphology on structure of dimeric surfactants. [J] Nature, 1993(362): 228-229). With the further discovery of the structural characteristics, excellent properties and structure-activity relationships of Gemini surfactants, these new surfactants have attracted the attention of scientists all over the world, and have attracted the attention of the industry, and they have made great efforts to seek their applications.

The gemini surfactant is formed by linking two surfactant molecules with a chemical bond structure, which effectively overcomes the same charge electrostatic repulsion of the ion head group and the repulsion of the hydration layer of the head group, and facilitates the close alignment of the surfactant ions. Compared with conventional surfactants, Gemini surfactants have very high surface activity, which is embodied in the following aspects: (1) it is easier for them to arrange closely at the gas/liquid surface, effectively reducing the surface tension of water; (2) it is easy for them to aggregate and form micelles, and have very low critical micelle concentration (cmc value), and the small critical micelle concentration also indicates that the solubilization of Gemini surfactant is better than that of traditional surfactant; (3) they form heteroform micelles at lower concentrations, so that the aqueous solution has special phase behavior and rheological property, which has special application in engineering; (4) they have a very low Krafft point, so that have a relatively low use temperature; (5) they can be compounded with common surfactants to produce a remarkable synergistic effect; (6) they has good dispersion property of calcium soap; and (7) they has excellent wettability.

The research on Gemini surfactants in China started late, and although there are many kinds of products at present, there are still some gaps in product development, performance research and application compared to foreign countries, especially in the search for raw materials with symmetrical structure per se, and its use in the synthesis of the Gemini surfactant with more excellent performance

SUMMARY OF THE INVENTION

It is an object of the present invention to provide a nonionic Gemini surfactant of (octylphenol polyoxyethylene ether disubstituted) dicarboxylic acid diphenyl ether and its synthesis method. The surfactant has high surface activity, and can by synthesized by simple methods under mild reaction conditions and is easy to separate and purify. The surfactant of the present invention is expected to be applied in tertiary oil recovery as an alkali/surfactant, in polymer/surfactant binary composite flooding, in alkali/surfactant/polymer ternary composite flooding, as a microemulsion emulsifier and the like, and it can also be compounded with a common surfactant to reduce the use cost and create conditions for its large-scale application.

To achieve the above objectives, the present invention provides the following technical solutions.

In one aspect, the present invention provides a nonionic Gemini surfactant of (octylphenol polyoxyethylene ether disubstituted) dicarboxylic acid diphenyl ether, and it has a structural formula as follows:

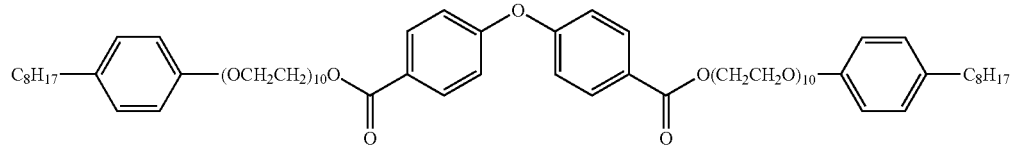

In another aspect, the present invention provides a synthesis method for the nonionic Gemini surfactant of (octylphenol polyoxyethylene ether disubstituted) dicarboxylic acid diphenyl ether, wherein the surfactant is synthesized by two steps. The reaction principle is as follows:

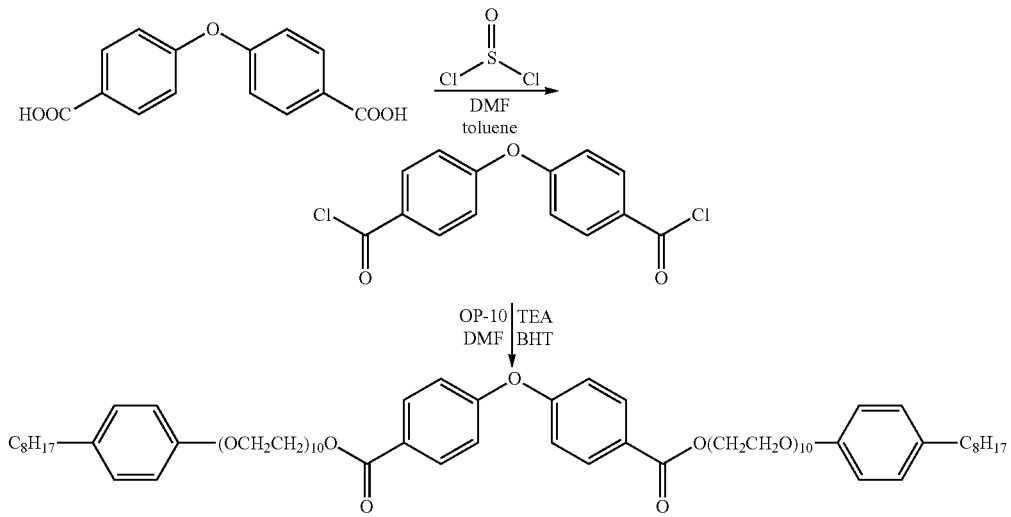

S1, diphenyl ether 4,4'-dicarboxylic acid is subjected to an acyl chlorination reaction to obtain diphenyl ether 4,4'-dicarbonyl dichloride;

S2, diphenyl ether 4,4'-dicarbonyl dichloride is subjected to an esterification reaction with octylphenol polyoxyethylene ether (OP-10) to obtain the target product, (octylphenol polyoxyethylene ether disubstituted) dicarboxylic acid diphenyl ether.

In that synthesis route, the original raw material diphenyl ether 4,4'-dicarboxylic acid is activated by acyl chlorination to obtain an intermediate product in the form of an acyl chloride; the acyl chloride is immediately subjected to an esterification reaction with a surfactant of octylphenol polyoxyethylene ether (OP-10) such that two molecules of OP-10 are attached to two symmetrical positions of the diphenyl ether, thus the target product, the non-ionic surfactant of (octylphenol polyoxyethylene ether disubstituted) dicarboxylic acid diphenyl ether, is obtained.

The preparation process of the present invention has only two steps, and the intermediate product obtained can be directly used in the next step without any purification treatment, which greatly simplifies the preparation process. The synthesis method is simple, the reaction conditions are mild and the product is easy to separate and purify.

The above synthesis steps will be described in detail below:

S1, diphenyl ether 4,4'-dicarboxylic acid is subjected to an acyl chlorination reaction to obtain diphenyl ether 4,4'-dicarbonyl dichloride.

There are many kinds of methods for acyl chlorination of carboxylic acid, such as thionyl chloride method, oxalyl chloride method, phosphorus trichloride method, phosphorus pentachloride method, etc. Among them, thionyl chloride is used to prepare the acyl chloride product under mild reaction conditions, and the reaction can be achieved at room temperature or slightly heated. All the products are gases except the acyl chloride, so it can be used without purification, the purity is good and the yield is high. In the examples of the invention, the thionyl chloride method is preferably adopted, in particular, diphenyl ether 4,4'-dicarboxylic acid is subjected to chlorination reaction with thionyl chloride, to obtain diphenyl ether 4,4'-dicarbonyl dichloride.

Further, the process of acyl chlorination reaction for diphenyl ether 4,4'-dicarboxylic acid with thionyl chloride comprises:

after the diphenyl ether 4,4'-dicarboxylic acid and N,N-dimethylformamide (DMF, catalyst) are added to a solvent, the thionyl chloride is added dropwise to the reaction system, after completion of the dropwise addition, the reaction is continued until the reaction is completed; then the reaction system is concentrated to dryness to give a brown solid intermediate, diphenyl ether 4,4'-dicarbonyl dichloride, which is used directly in the next reaction.

As the catalyst for the acyl chlorination reaction, N,N-dimethylformamide may be used in a catalytic amount of the general reaction, and there is no strict requirement. In a preferred embodiment of that present invention, the molar ratio of diphenyl ether 4,4'-dicarboxylic acid to DMF is 1: (0.1 to 0.2). In addition, the catalyst which can be used in the method of acyl chlorination by thionyl chloride may be N,N-dimethylaniline, pyridine, or the like.

Many solvents can be used in the reaction, such as one or more of dichloromethane, trichloromethane, benzene or toluene or their mixture, and toluene is used as the solvent for the acyl chlorination reaction in a preferred embodiment of the present invention.

Preferably, the thionyl chloride is used in an amount slightly excess with respect to the carboxylic acid in order to ensure that the chlorination can be carried out as completely as possible. In the invention, the molar ratio of diphenyl ether 4,4'-dicarboxylic acid to thionyl chloride is 1: (2.1 to 2.2). The process of acyl chlorination is rather violent, so the dropwise addition of thionyl chloride to the reaction system should be slow, preferably controlled to 1 to 2 drops/sec. If the temperature of the system is high at the time of dropwise addition, the dropwise addition speed should be slower. The dropwise addition speed can be adjusted by an experimental personnel according to the phenomenon during operation, and the experimental personnel should pay attention to the safety of the test.

Preferably, in order to reduce by-products and improve the reaction yield, the acyl chlorination reaction is carried out under an atmosphere of protective gas. More preferably, the protective gas comprises nitrogen and an inert gas. The inert gases are for example helium and argon.

Preferably, after the dropwise addition of thionyl chloride is completed, the reaction is continued at an elevated temperature. In order to accelerate that reaction speed when the temperature is elevated, the reaction can be performed under room temperature or slightly heating conditions and because the reaction itself is fast. The specific heat temperature can be adjusted according to the selected specific solvent. In a preferable embodiment of the present invention, the reaction is carried out by elevating the temperature to 70° C.

S2, diphenyl ether 4,4'-dicarbonyl dichloride is subjected to an esterification reaction with OP-10 to obtain the target product, (octylphenol polyoxyethylene ether disubstituted) dicarboxylic acid diphenyl ether.

Preferably, the step of S2 comprises:
dissolving diphenyl ether 4,4'-dicarbonyl dichloride in a first solvent to obtain a first solution;
adding OP-10, N,N-dimethylformamide, triethylamine, and 2,6-di-tert-butyl-4-methylphenol as an antioxidant to a second solvent to obtain a second solution;
slowly and dropwise adding the first solution to the second solution to carry out an esterification reaction; and
after completion of the reaction, performing a post-treatment purification to obtain the target product, (nonylphenol polyoxyethylene ether disubstituted) dicarboxylic acid diphenyl ether.

The first solvent and the second solvent may be selected from a plurality of commonly used organic solvents, and may be the same or different. Preferably, the first solvent is dichloromethane. Preferably, the second solvent is also dichloromethane.

In this reaction, OP-10 is used in an amount slight excess with respect to the acyl chloride in order to ensure that the acyl chloride is linked to the surfactant OP-10 by esterification as much as possible. Preferably, the molar ratio of OP-10 to diphenyl ether 4,4'-dicarbonyl dichloride is (2.1 to 2.2): 1.

Preferably, the molar ratio of N,N-dimethylformamide to diphenyl ether 4,4'-dicarbonyl dichloride is (0.1 to 0.2): 1.

Preferably, the molar ratio of triethylamine as a base to diphenyl ether 4,4'-dicarbonyl dichloride is (2.1 to 2.2): 1.

Preferably, the molar ratio of 2,6-di-tert-butyl-4-methylphenol (BHT) as an antioxidant to diphenyl ether 4,4'-dicarbonyl dichloride is (0.1 to 0.2): 1. In the course of the reaction, BHT is first esterified with acyl chloride and then substituted with OP-10 alcohol to prevent self-condensation of the raw material.

In a preferred embodiment of the invention, S2 specially comprises:
dissolving one molar equivalent of diphenyl ether 4,4'-dicarbonyl dichloride in a solvent to obtain a first solution;
adding and dissolving (2.1 to 2.2) molar equivalent of OP-10, (0.1 to 0.2) molar equivalent of N,N-dimethylformamide (DMF), (2.1 to 2.2) molar equivalent of triethylamine(TEA) and (0.1 to 0.2) molar equivalent of 2,6-di-tert-butyl-4-methylphenol (BHT) as an antioxidant into a second solvent to obtain a second solution;
slowly and dropwise adding the first solution to the second solution to carry out an esterification reaction; and
after completion of the reaction, performing a post-treatment purification to obtain the target product, (nonylphenol polyoxyethylene ether disubstituted) dicarboxylic acid diphenyl ether.

Preferably, the post-treatment purification comprises: quenching with water; separating the liquid; recovering the organic phase, which is concentrated to dryness; and performing a purification by column chromatography purification, to obtain the target product..

Preferably, the developing agent in the purification by column chromatography is a system of petroleum ether and ethyl acetate. More preferably, V (petroleum ether):V (ethyl acetate)=10:1.

The reaction end point in the synthesis method of the present invention is monitored using TLC.

The present invention has the follow advantageous effects over the prior art:

The present invention provides a novel surfactant: a nonionic Gemini surfactant of (octylphenol polyoxyethylene ether disubstituted) dicarboxylic acid diphenyl ether, which has not been reported in the literature.

The inventive synthesis method is simple, the synthesis steps are composed of an acyl chlorination reaction and a one-step esterification reaction, the reaction conditions are mild, the operation is simple, and it is easy for the product to separate and purify.

The target product of the present invention has excellent surface activity, it has a critical micelle concentration of 0.01 wt %, which is a quarter of the non-ionic surfactant OP-10 (cmc=0.04 wt %); and has a surface tension at critical micelle concentration of 30 mN/m, lower than OP-10 ($\gamma_{cmc}$=32 mN/m) by 2 mN/m.

DETAILED DESCRIPTION

In order to more clearly illustrate the present invention, the present invention will be further described in connection with preferable examples. It will be understood by those skilled in the art that the following detailed description is illustrative but not limiting, and should not be used to limit the scope of the invention.

Preparation of (octylphenol polyoxyethylene ether disubstituted) dicarboxylic acid diphenyl ether (1) Synthesis of diphenyl ether 4,4'-dicarbonyl dichloride Into a three-necked flask placed in a constant temperature water bath and equipped with an agitator, 2 g (7.75 mmol) of diphenyl ether 4,4'-dicarboxylic acid and 0.113 g (1.55 mmol) of DMF (catalyst) were added, and 50 mL of toluene as solvent was further added under the protection of nitrogen. After that, 2.03 g (17.04 mmol) of thionyl chloride was slowly added dropwise, and stirred. After completion of the dropwise addition, the temperature is raised up to 70° C., and the reaction processed for 4 h (the end point of the reaction is monitored by TLC). After completion of the reaction, the reaction was concentrated to dryness to give a brown solid intermediate, diphenyl ether 4,4'-dicarbonyl dichloride which was used directly in the next reaction.

(2) Synthesis of (octylphenol polyoxyethylene ether disubstituted) dicarboxylic acid diphenyl ether 2.7 g (9.15 mmol) of diphenyl ether 4,4'-dicarbonyl dichloride is dissolved in a certain amount of methylene chloride. 13.02 g (20.13 mmol) of OP-10, 0.134 g (1.83 mmol) of DMF, 2.04 g (20.13 mmol) of TEA (triethylamine) and 0.403 g (1.83 mmol) of BHT (2,6-di-tert-butyl-4-methylphenol) as an antioxidant were added into a three-necked flask equipped with an agitator, and a certain amount of methylene chloride was added therein to dissolve the raw materials. Into the three-necked flask, the diphenyl ether 4,4'-dicarbonyl dichloride in methylene chloride was slowly added dropwise, and the reaction was performed at room temperature for 4 h (the end point of the reaction is monitored by TLC). After completion of the reaction, water was added to quench, the liquid was separated, the organic phase was recovered, and concentrated to dryness, and purified by a column (at a condition of V (petroleum ether):V (ethyl acetate) EA=10:1). Thus, 8.3 g (5.49 mmol) of a brown oil-like product, (octylphenol polyoxyethylene ether disubstituted) dicarboxylic acid diphenyl ether, was obtained.

Figure 1:
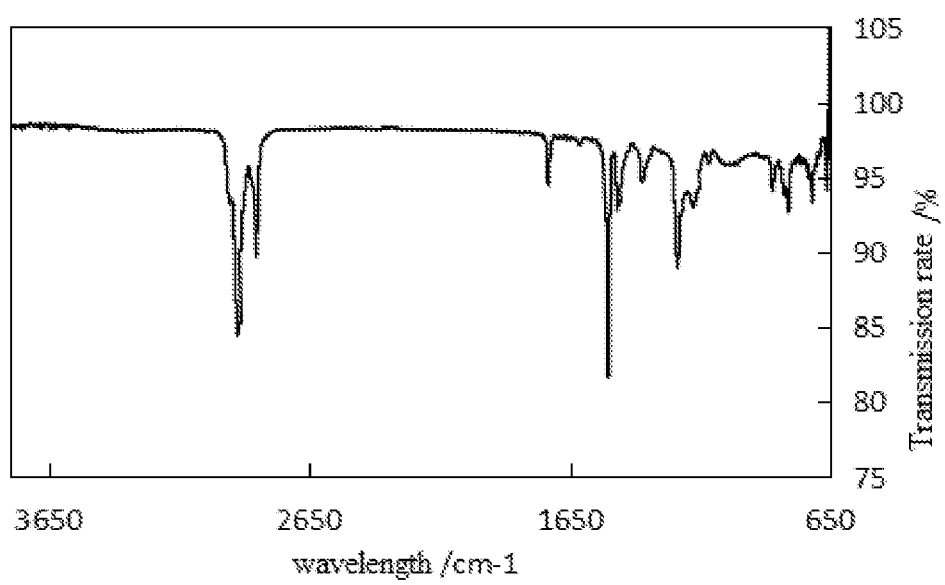
FIG. 1 is an infrared spectrum of (octylphenol polyoxyethylene ether disubstituted) dicarboxylic acid diphenyl ether prepared in the examples of the present invention.

An infrared spectrum of (octylphenol polyoxyethylene ether disubstituted) dicarboxylic acid diphenyl ether The infrared spectrum of the obtained target product is shown in FIG. 1, and it can be seen from the analysis of the spectrum that:

2924, 2848 are $CH_3$, $CH_2$ extensional vibration peaks; 1501, 1466 are vibrational peaks of the benzene ring skeleton; 872, 811 are characteristic peaks of para-substitution of benzene ring; 1728 is C=O extensional vibration peak; 1105 is C—O extensional vibration peak.

Figure 2:
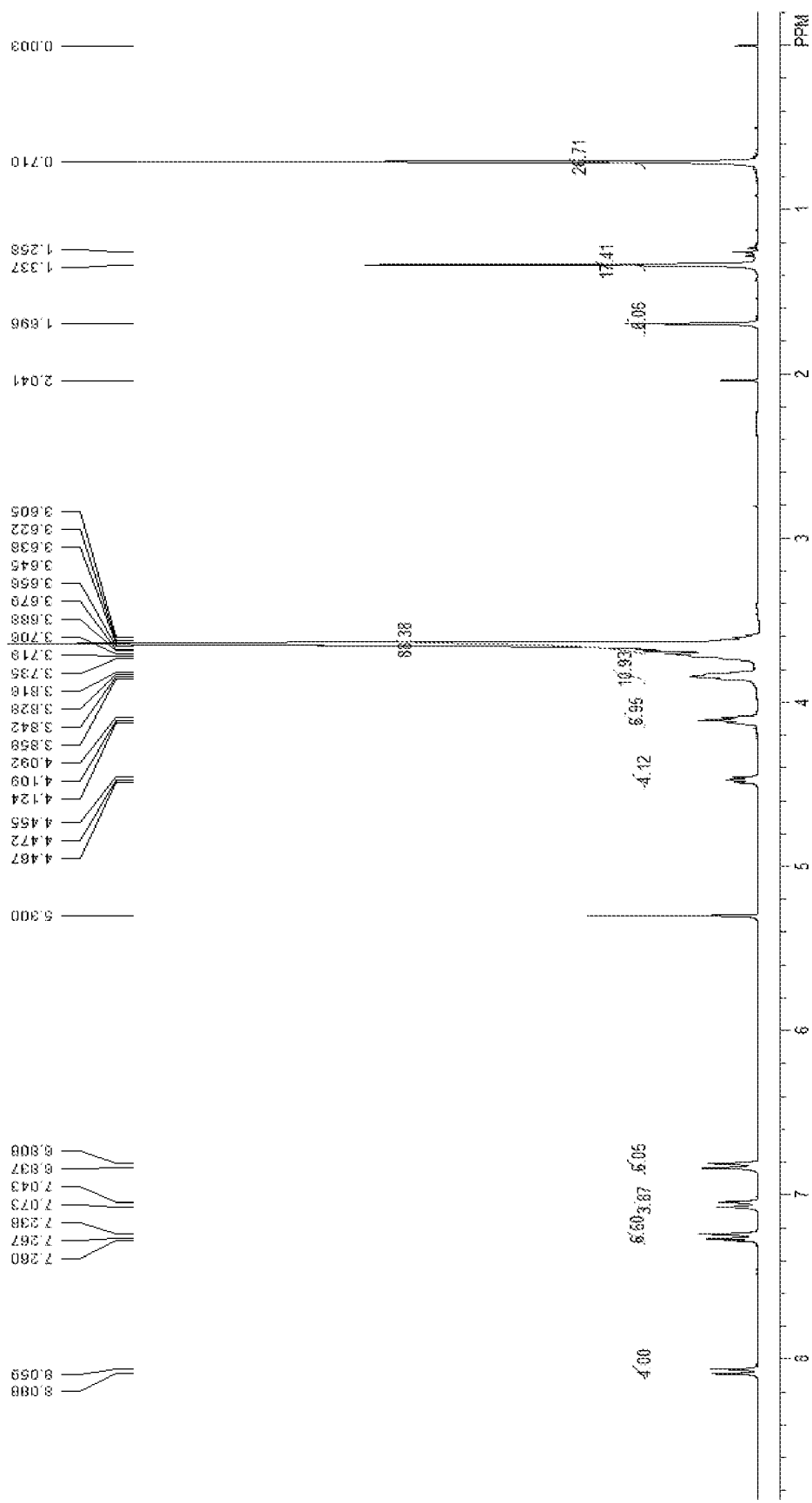
FIG. 2 is a nuclear magnetic hydrogen spectrum of (octylphenol polyoxyethylene ether disubstituted) dicarboxylic acid diphenyl ether prepared in the examples of the present invention.

A nuclear magnetic hydrogen spectrum of (octylphenol polyoxyethylene ether disubstituted) dicarboxylic acid diphenyl ether The nuclear magnetic hydrogen spectrum of the obtained target product is shown in FIG. 2, and it can be seen from the analysis of the spectrum that:

$^1$H-NMR(400 MHz, $CDCl_3$): δ: 0.71 [3H, $CH_3CH_2$], 1.25-1.33 [10H, $CH_3(CH_2)_5CH_2CH_2$], 1.69 [2H, $(CH_3(CH_2)_5CH_2CH_2]$, 2.04 [2H, $CH_3(CH_2)_5CH_2CH_2$], 3.60-3.68 [16H, $(CH_2CH_2O)_8CH_2CH_2OC$], 3.70-3.73 [2H, $(CH_2CH_2O)_8CH_2CH_2OC$], 3.81-3.85 [2H, $(CH_2CH_2O)_8CH_2CH_2OC$], 4.09-4.12 [2H, $COOCH_2CH_2O(CH_2CH_2O)_8$], 4.45-4.48 [2H, $COOCH_2CH_2O(CH_2CH_2O)_8$], 7.04-7.28 [1H, CHCHCCOO], 8.05-8.08 [1H, CHCHCCOO].

Figure 3:
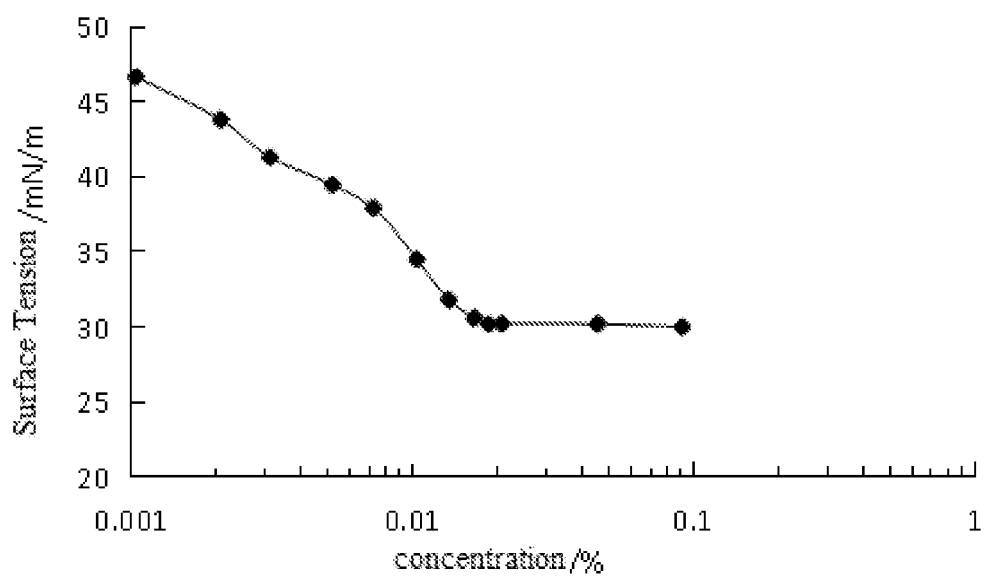
FIG. 3 is a graph of surface tension versus concentration (25° C.) of (octylphenol polyoxyethylene ether disubstituted) dicarboxylic acid diphenyl ether prepared in in the examples of the present invention.

Surface Activity Determination of (octylphenol polyoxyethylene ether disubstituted) dicarboxylic acid diphenyl ether The ability of surfactant to reduce the surface tension of water is an important parameter to evaluate its surface activity. The surface tension of aqueous solution of target product at different concentration at 25° C. is determined by a hanging plate method, and a concentration dependent curve was made for the surface tension of an aqueous solution of (octylphenol polyoxyethylene ether disubstituted) dicarboxylic acid diphenyl ether Gemini surfactant (FIG. 3). From this curve, the surface activity parameters of the Gemini surfactant can be obtained, that is, the critical micelle concentration cmc is 0.01 wt %, and the surface tension cmc at the critical micelle concentration is 30 mN/m.

It will be apparent that the above-described examples of the present invention are merely for clearly illustration of the present invention and are not intended to limit the embodiments of the present invention. To those of ordinary skill in the art, other different forms of changes or variations may also be made on the basis of the above description. It is unable to exhaust all implementations, and the obvious changes or variations that are introduced from the technical solution of the present invention are still within the scope of the present invention.

What is claimed is:

1. A nonionic Gemini surfactant of (octylphenol polyoxyethylene ether disubstituted) dicarboxylic acid diphenyl ether, having the structural formula:

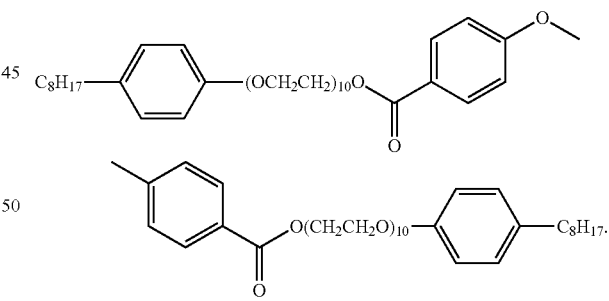

* * * * *